United States Patent [19]

Rose et al.

[11] 4,402,699
[45] Sep. 6, 1983

[54] COUPLER COMPONENTS FOR THE OXIDATION OF HAIR DYES AND THEIR USE, AS WELL AS HAIR DYEING AGENTS CONTAINING THEM

[75] Inventors: David Rose, Hilden; Norbert Maak, Neuss, both of Fed. Rep. of Germany

[73] Assignee: Henkel Kommanditgesellschaft auf Aktien, Düsseldorf-Holthausen, Fed. Rep. of Germany

[21] Appl. No.: 258,523

[22] Filed: Apr. 28, 1981

[30] Foreign Application Priority Data

May 2, 1980 [DE] Fed. Rep. of Germany ........ 3016906

[51] Int. Cl.$^3$ ..................... A61K 7/13; C07C 119/06
[52] U.S. Cl. ........................................ 8/412; 564/276; 564/275
[58] Field of Search ................. 564/276, 272, 275; 8/412; 260/501.17

[56] References Cited

U.S. PATENT DOCUMENTS 4,126,461 11/1978 Pupo et al. .................... 430/525
4,198,349 4/1980 Nuss et al. .................... 564/272

FOREIGN PATENT DOCUMENTS 2509096 9/1976 Fed. Rep. of Germany .

*Primary Examiner*—Natalie Trousof
*Assistant Examiner*—L. Hendriksen
*Attorney, Agent, or Firm*—Fisher, Christen & Sabol

[57] ABSTRACT

2,4-Dichloro-3-alkylidene-aminophenols having the formula:

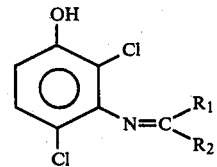

wherein $R_1$ represents hydrogen or an alkyl radical having 1 to 6 carbon atoms and $R_2$ represents an alkyl radical having 1 to 6 carbon atoms or an aryl radical, with the proviso that $R_2$ can only be an aryl radical when $R_1$ is hydrogen.

The 2,4-dichloro-alkylidene-aminophenols can be produced by reaction of 2,4-dichloro-3-aminophenol with the corresponding aldehydes or ketones. They are suitable as such, or in the form of their salts with inorganic or organic acids, as coupler components in oxidation hair dyes.

15 Claims, No Drawings

COUPLER COMPONENTS FOR THE OXIDATION OF HAIR DYES AND THEIR USE, AS WELL AS HAIR DYEING AGENTS CONTAINING THEM

BACKGROUND OF THIS INVENTION

1. Field of this Invention

This invention relates to coupler components for the oxidation of hair dyes, hair dyes containing such coupler components and the use of such coupler components.

2. Prior Art

The so-called oxidation colors, which develop by the oxidative coupling of a developer component with a coupler component, play a preferred role for the dyeing of hair because of their intensive colors and very good fastness characteristics. Customarily nitrogen bases, such as, p-phenylene diamine derivatives, diaminopyridines, 4-amino pyrazolone derivatives and heterocyclic hydrazones, are used as developer substances. m-Phenylene diamine derivatives, phenols, naphthols, resorcin derivatives and pyrazolones are examples of so-called coupler components.

BROAD DESCRIPTION OF THIS INVENTION

An object of this invention is to provide new coupler components for the oxidation of hair dyes. Another object of this invention is to provide hair dyes containing such new coupler components. A further invention is to provide a process for the use of such new coupler components. Other objects and advantages of this invention are set out herein or are obvious herefrom to one ordinarily skilled in the art.

The objects and advantages of this invention are achieved by the compounds, compositions and processes of this invention.

This invention involves 2,4-dichloro-3-alkylidene-aminophenols having the formula:

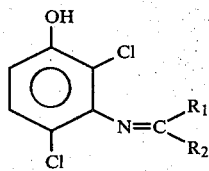

wherein $R_1$ represents hydrogen or an alkyl radical having 1 to 6 carbon atoms and $R_2$ represents an alkyl radical having 1 to 6 carbon atoms or an aryl radical, with the proviso that $R_2$ can only be an aryl radical when $R_1$ is hydrogen. Processes for their production are disclosed. Preferably $R_1$ and $R_2$, which may be the same or different, is an alkyl radical having 1 to 4 carbon atoms.

The production of the 2,4-dichloro-3-alkylidene-amino-phenols can be accomplished by extended heating of 2,4-dichloro-3-aminophenol with compounds having the formula:

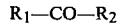

$$R_1-CO-R_2$$

wherein $R_1$ and $R_2$ have the same meaning as stated above.

Compounds having the formula $R_1COR_2$ are preferably used in an excess, whereby the excess of such compound simultaneously also serves as solvent. The process can also be carried out in the presence of other solvents, such as, alcohols or chlorinated hydrocarbons. The reactants are boiled for a short time under reflux or are allowed to react for a few hours at 0° to 50° C.

The conversion is effectively carried out in the presence of at least one catalyst which favors separation of water. Such catalysts are advantageously mineral acids, such as, HCl and $H_2SO_4$, as well as toluene sulfonic acid and others. HCl is the preferred catalyst.

Examples of aryl groups are phenyl and naphthyl.

Examples of alkyl groups are methyl, ethyl, butyl, isobutyl, propyl, isopropyl, secondary butyl, tertiary butyl, 1-pentyl, 2-methyl-1-butyl, isoamyl, 2-pentyl, 3-pentyl, 3-methyl-2-butyl, 2-methyl-2-butyl, 1-hexyl, 2-methyl-1-pentyl, 3-methyl-1-pentyl, isohexyl, 2-ethyl-1-butyl, 2-hexyl, 3-hexyl, 2,3-dimethyl-1-butyl and 3-methyl-2-pentyl.

Compounds having the formula $R^1-CO-R^2$ are for example ketones, such as, acetone, methyl ethyl ketone, 2-pentanone, 3-methyl-2-butanone, 3-pentanone, 2-hexanone, 3-hexanone, methyl isobutyl ketone, 2-methyl-3-pentanone, 3-methyl-2-pentanone, methyl t-butyl ketone, dipropyl ketone, diisopropyl ketone, di-isobutyl ketone and hexamethylacetone.

When the compounds of the formula $R^1-CO-R^2$ are used in an excess for example, up to 20 or so moles of such compounds are used per mole of the 2,4-dichloro-3-aminophenol, whereby at the same time they serve as solvent and reactant.

When the coupler components of this invention are produced in the presence of solvents, examples of useful alcohol solvents are methanol, ethanol, butanol, isopropanol, propanol and isobutanol, and examples of useful chlorinated hydrocarbons are carbon tetrachloride, 1,2-dichloroethane, 1-chlorobutane, 2-chlorobutane, 1,1-dichloroethane, 1,1,2,2-tetrachloroethane, 1,1,1,2-tetrachloroethane, 1,4-dichlorobutane, 2,2-dichlorobutane, 2,3-dichlorobutane, 1-chloropropane, pentachloroethane, 1,1,1-trichloroethane, 1-chloropentane, 1,1,2-trichloroethane, 1,1-dichlorobutane, 1,2-dichlorobutane, 1,3-dichlorobutane, 1,1,1,2-tetrachlorobutane, 1,2-dichloropropane, 1,3-dichloropropane, 2,2-dichloropropane, 1,1,3-trichloropropane, 1,1,1,2-tetrachloropropane and 2-chloropentane.

This invention also involves the process of using the new 2,4-dichloro-3-alkylidene-aminophenols as such, or in the form of their salts with inorganic or organic acids, as coupler components in oxidation hair dyes, which therefor contain the new 2,4-dichloro-3-alkylidene-aminophenols of this invention.

Good oxidation hair dyestuff components, in the first place, must fulfill the following assumptions:

During the oxidative coupling with the pertinent developer or coupler components, they must develop the desired color nuances in sufficient intensity. They must furthermore have a sufficient-to-very good attachment capacity on human hair, and beyond that they are supposed to be unobjectionable from a toxicological and dematological point of view.

Therefore, in the search for useable oxidation hair dyestuff, there was the task of discovering suitable components which optimally fulfill the aforegoing assumptions.

This invention is based, in part, on the discovery that oxidation hair dyes to a particularly high degree fulfill the requirements set forth above for them whenever the coupler components in them are 2,4-dichloro-3-alkylidene-aminophenols having the formula:

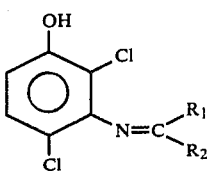

wherein $R_1$ represents hydrogen or an alkyl radical having 1 to 6 carbon atoms and $R_2$ represents an alkyl radical having 1 to 6 carbon atoms or an aryl radical, provided that $R_2$ is only an aryl radical when $R_1$ is hydrogen, as well as salts thereof with organic or inorganic acids, in combinations with the customary developer substances.

Hair dyeing agents on the basis of oxidation colors containing at least one 2,4-dichloro-3-alkylidene-aminophenol having the formula:

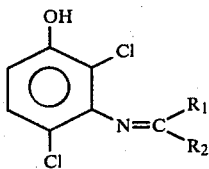

wherein $R_1$ and $R_2$ have the same meaning as stated above, as well as salts thereof with inorganic or organic acids, as coupler components, and at least one developer substances customary used in oxidation hair dyes, therefore, represent valuable compositions in the field of oxidation hair dyes.

When used as coupler components, the compounds of this invention, along with the developer substances used generally for oxidation hair dyeing, produce very intensive color tones reaching from brown, over dark blue to dark violet-thus they represent an essential enrichment of oxidative hair dyeing possibilities. Beyond that, the 2,4-dichloro-3-alkylene-aminophenols of this invention are distinguished by the very good fastness characteristics of the colorations achieved with them, by their good solubility in water and by their good storage stability, as well as their lack of any toxicological and dermatological objectionableness.

The 2,4-dichloro-3-alkalidene-aminophenols, used according to this invention as coupler components, can be used either as such or in the form of their salts with inorganic or organic acids, such as, chlorides, sulfates, phosphates, acetates, propionates, lactates and citrates.

The preferred coupler components of this invention are 2,4-dichloro-3-(4-methylpentylidene-2)-aminophenol, 2,4-dichloro-3-(isopropylidene)-aminophenol and 2,4-dichloro-3-benzylidene-aminophenol.

Examples of the developer components useful in the hair dyeing agents of this invention are the primary aromatic amines having an additional functional group, in the p-position, such as, p-phenylenediamine, p-toluylenediamine, p-aminophenol, N-methyl-p-phenylenediamine, N,N-dimethyl-p-phenylenediamine, N-ethyl-N-hydroxyethyl-p-phenylenediamine, chloro-p-phenylenediamine, N,N-bis-hydroxyethylamino-p-phenylenediamine, methoxy-p-phenylenediamine, 2-chloro-p-phenylenediamine, 2,6-dichloro-p-phenylenediamine, 2-chloro-6-bromo-p-phenylenediamine, 2-chloro-6-methyl-p-phenylenediamine and 6-methoxy-3-methyl-p-phenylenediamine. Other examples are other compounds of the type mentioned above which further represent one or more functional group, such as, OH—groups, $NH_2$—groups, NHR—groups and $NR_2$—groups, wherein R represents an alkyl radical having 1 to 4 carbon atoms. Further examples are diaminopyridine derivatives, heterocyclic hydrazone derivatives, such as, 1-methyl-pyrrolidone-(2)-hydrazone, 4-aminopyrazolone derivatives, such as, 4-amino-1-phenyl-3-carbamoylpyrazolone-5-, N-butyl-N-sulfobutyl-p-phenylenediamine, and tetraminopyrimidines, such as, 2,4,5-6-tetraaminopyrimidine, 4,5-diamino-2,6-bis-methylaminopyrimidine, 2,5-diamino-4-diethylamino-6-methylaminopyrimidine, 2,4,5-triamino-6-dimethylaminopyrimidine, 2,4,5-triamino-6-piperidinopyrimidine, 2,4,5-triamine-6-anilino-pyrimidine, 2,4,5-triamino-6-anilino-pyrimidine, 2,4,5-triamino-6-morpholinopyrimidine and 2,4,5-triamino-6-$\beta$-hydroxyethylamino-pyrimidine.

Besides other shades of colors, the coupler components of this invention, with the corresponding developer substances, produce especially-intense dark-blue hair dyes which excel in having extraordinary light fastness. They are, therefore, also of particular importance as a shading component for achieving as strong as possible hues, which largely corresponding to the natural hair dye shades, since difficulties often arise in the case of the production of natural color shades with the help of blue coupler components.

In hair dyeing agents, the coupler components of this invention are generally used in about molar quantities, related to the developer substances used. Whenever the use of molar quantities proves to be effective, it is not then disadvantageous to use the coupler component at a certain excess at a certain deficiency.

Furthermore, it is not necessary that the developer component and the coupler substance be homogeneous products. Rather the developer component can be mixtures of the developer compounds which can be used according to this invention, and the coupler substance can be mixtures of the 2,4-dichloro-3-alkylidene-aminophenols of this invention, in some cases being mixed with other customary coupler substances.

Beyond that, in case it is necessary in order to achieve certain shades, the hair dyes of this invention can possibly contain customary directly drawing dyes in a mixture.

In the case of oxidative coupling, the development of the coloration can basically also be achieved by the oxygen in the air as is the case of with other oxidation hair dye dyestuffs. Preferably, however, chemical oxidizing agents are used. The preferred chemical oxidizing agents are hydrogen peroxide and its addition-products with urea melamine and sodium borate; other examples are mixtures from such hydrogen peroxide-addition compounds with potassium peroxide disulfate.

The hair dyes of this invention, to be in marketable forms, are usually worked into corresponding cosmetic preparations, such as, ointments, emulsions or even simple solutions, and immediately prior to their use on the hair are mixed with one of the cited oxidation agents. The concentration, in such coloring preparations, of the coupler-developer combination is 0.2 to 5 percent by weight, preferably 1 to 3 percent by weight. For the production of ointments, emulsions or jells, the dyestuff components are mixed with additional components customarily used in such preparations. Examples of such additional components are wetting agents or emulsifying agents of the anionic and non-ionogenic type, such as, alkylbenzol sulfonates, fatty alcohol sulfates, alkyl sulfonates, fatty acid alkanol amides and addition-products of ethylene oxide to fatty alcohols, thickeners, such as, methylcellulose, starch, higher fatty alcohols, paraffin oil and fatty acids, scented oils and hair care agents, such as, pantothenic acid and cholesterol. The additives cited are used in the quantities customary for their purposes, for example, wetting agents and emulsifiers are used in concentrations of 0.5 to 30 percent by weight and thickeners are used in concentrations of 0.1 to 25 percent by weight, always related to the entire preparation.

The use of the hair dyes of this invention can be accomplished in a weakly acid environment, or a neutral environment or especially an alkaline environment having a pH value of 8 to 10. The application temperatures are in the range from 15° to 40° C. After an application or action time of about 30 minutes, the hair dyeing agent is removed by rinsing from the hair being dyed. After that, the hair is washed secondarily with a mild shampoo and dried.

The colorations obtainable with the hair dyes of this invention, especially the bluish shades, show particularly intensive nuances of color with the use of variable developer and coupler components. The resultant colorations have good fastness characteristics as to light, washing and friction and can easily be removed when desired with reducing agents.

DETAILED DESCRIPTION OF THIS INVENTION

The following examples explain the objects of this invention in more detail, without however limiting this invention thereto.

EXAMPLE 1

2,4-dichloro-3-(4-methylpentylidene-2)-aminophenol hydrochloride 5 g of 2,4-dichloro-3-aminophenol-hydrochloride (produced according to the data and procedure set out in the German O. S. No. 2,509,096, the pertinent parts of which are incorporated herein by reference, was boiled in 50 ml of methyl isobutyl ketone for half an hour under reflux. After cooling down, the product was drawn off and dried. The 2,4-dichloro-3-(4-methylpentylidene-2)-aminophenol hydrochloride had the following IR-adsorption spectrum: IR-spectrum (KBr)cm$^{-1}$: 1650, 1620, 1520, 1475, 1435, 1370, 1315, 1260, 1215, 1180, 1090, 1045, 1010, 980, 970, 825, 815, 790, 785, 760, 690.

EXAMPLE 2

2,4-dichloro-3-(isopropylidene)-aminophenol hydrochloride

Corresponding to the procedure and data in Example 1, 2,4-dichloro-3-aminophenol hydrochloride was reacted with acetone. The reaction product obtained according to this example of this invention had the following characteristic data: IR-spectrum (KBr) cm$^{-1}$ 1652, 1598, 1570, 1480, 1438, 1370, 1315, 1260, 1238, 1225, 1218, 1176, 1112, 1085, 1010, 980, 930, 870, 835, 805, 762, 730, 710, 675, 655.

EXAMPLE 3

2,4-dichloro-3-benzylidene-aminophenol hydrochloride

Analogously to the procedure and data in Examples 1 and 2, 2,4-dichloro-3-aminophenol hydrochloride was reacted with benzaldehyde. The reaction product of this example of this invention had the following characteristic data: IR-spectrum (Kbr) cm$^{-1}$: 1692, 1620, 1598, 1582, 1515, 1480, 1450, 1430, 1310, 1205, 1160, 1075, 1030, 930, 905, 890, 872, 830, 805, 745, 700, 685, 650.

The previously-mentioned 2,4-dichloro-3-alkylideneaminophenols, their production being described in Examples 1, 2 and 3, were used as coupler components in the following experiments.

EXAMPLES 4–16

The following substances served as developer components:
E1: p-toluylenediamine
E2: 2,4,5,6-tetraaminopyrimidine
E3: 2-piperidino-4,5,6-triaminopyrimidine
E4: 2-methylamino-4,5,6-triaminopyrimidine
E5: 2-morpholino-4,5,6-triaminopyrimidine
E6: p-phenylenediamine
E7: 2-chloro-p-phenylenediamine
E8: p-aminophenol
E9: N-methyl-p-phenylenediamine
E10: N-ethyl-N-$\beta$-hydroxyethyl-p-phenylenediamine
E11: N,N-bis($\beta$-hydroxymethyl)-amino-p-phenylenediamine.

The hair dyeing agents of this invention were used in the form of ointment emulsions. At the same time, into an emulsion of:

(a) 10 parts by weight of fatty alcohols having chain lengths of $C_{12}$ to $C_{18}$;

(b) 10 parts by weight of fatty alcohol sulfates (sodium salt) having a chain length of $C_{12}$ to $C_{18}$; and (c) 75 parts by weight of water, 0.01 mole of the developer and coupler substances listed in following Table 1 was always worked in. After that, the pH value of the emulsion was adjusted by means of ammonia to 9.5 and the emulsion was made up with water to 100 parts by weight. The oxidative coupling was carried out with 1-percent hydrogen peroxide solution as the oxidation agent, whereby 10 parts by weight of the hydrogen peroxide solution were added to 100 parts by weight of the emulsion. The pertinent coloring ointment was applied to 90-percent graying not-especially-pretreated human hair, with the addition of oxidation agents, and was left there for 30 minutes. After completion of the dyeing process the hair was washed with a customary shampoo and was subsequently dried. The colorations obtained thereby are set out in following Table 1:

TABLE 1

| Example No. | Developer | Coupler of Example | Color Shade Obtained Using 1% H$_2$O$_2$ Solution |
|---|---|---|---|
| 4 | E | 1 | 1 | dark violet |
| 5 | E | 1 | 2 | dark blue |
| 6 | E | 2 | 2 | blue |
| 7 | E | 3 | 2 | olive |
| 8 | E | 4 | 2 | bluish gray |
| 9 | E | 5 | 2 | gray turquoise |
| 10 | E | 6 | 2 | dark violet |
| 11 | E | 7 | 2 | aubergine |
| 12 | E | 8 | 2 | brown |
| 13 | E | 9 | 2 | blue-black |
| 14 | E | 10 | 2 | blue-black |
| 15 | E | 11 | 2 | dark blue |
| 16 | E | 1 | 3 | grayish brown |

What is claimed is:

1. 2,4-dichloro-3-alkylidene-aminophenol having the formula:

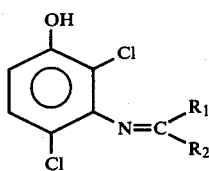

wherein $R_1$ is hydrogen or an alkyl radical having 1 to 6 carbon atoms and $R_2$ is an alkyl radical having 1 to 6 carbon atoms, or a salt thereof with an organic acid or inorganic acid.

2. The 2,4-dichloro-3-alkylidene-aminophenol as claimed in claim 1 wherein $R_1$ and $R_2$ are each an alkyl radical having 1 to 6 carbon atoms.

3. The 2,4-dichloro-3-alkylidene-aminophenol as claimed in claim 1 wherein $R_1$ is hydrogen.

4. The 2,4-dichloro-3-alkylidene-aminophenol as claimed in claim 1 which is 2,4-dichloro-3-(4-methyl-pentylidene-2)-aminophenol.

5. The 2,4-dichloro-3-alkylidene-aminophenol as claimed in claim 1 which is 2,4-dichloro-3-(isopropylidene)-aminophenol.

6. 2,4-dichloro-3-alkylideneaminophenol having the formula:

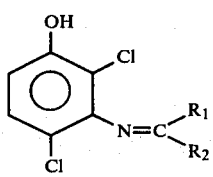

wherein $R_1$ and $R_2$ can be the same or different and each is an alkyl radical having 1 to 4 carbon atoms, or a salt thereof with an organic acid or inorganic acid.

7. Hair dyeing agent based upon oxidation hair dyes comprising at least one 2,4-dichloro-3-alkylidene-aminophenol, or salt thereof with an inorganic or organic acid, as claimed in claim 1, as the coupler component, and the developer components of oxidation hair dyes.

8. Hair dyeing agent based upon oxidation hair dyes comprising at least one 2,4-dichloro-3-alkylidene-aminophenol, or salt thereof with an inorganic or organic acid, as claimed in claim 2, as the coupler component, and the developer components of oxidation hair dyes.

9. Hair dyeing agent as claimed in claim 7 or claim 8 wherein the amount of developer-coupler components is 0.2 to 5 percent by weight, related to the weight of the entire hair dyeing agent.

10. Hair dyeing agent as claimed in claim 9 wherein the amount of developer-coupler components is 1 to 3 percent by weight, related to the weight of the entire hair dyeing agent.

11. Process of preparing an oxidation hair dye which comprises mixing at least one 2,4-dichloro-3-alkylidene-aminophenol, or salt thereof with an organic or inorganic acid, as claimed in claim 1, as the coupler component, and the developer components of oxidation hair dyes.

12. Process of preparing an oxidation hair dye which comprises mixing at least one 2,4-dichloro-3-alkylidene-aminophenol, or salt thereof with an inorganic or organic acid as claimed in claim 6, the coupler component and the developer components of oxidation hair dyes.

13. Process of dyeing hair using the oxidation hair dye of claim 7.

14. Process of dyeing hair using the oxidation hair dye of claim 8.

15. The 2,4-dichloro-3-alkylidene-aminophenol as claimed in claim 1 wherein the salt thereof is with hydrogen chloride.

* * * * *